United States Patent
Hoffmann et al.

(10) Patent No.: US 11,185,614 B2
(45) Date of Patent: Nov. 30, 2021

(54) BALLOON CATHETER COATED WITH AN ANTI-RESTENOTIC ACTIVE INGREDIENT AND A MOLECULAR DISPERSION AGENT THAT PROMOTES TRANSPORT

(75) Inventors: Erika Hoffmann, Eschweiler (DE); Michael Hoffmann, Eschweiler (DE); Roland Horres, Stolberg (DE)

(73) Assignee: Hemoteq AG, Würselen (DE)

( * ) Notice: Subject to any disclaimer, the term of this patent is extended or adjusted under 35 U.S.C. 154(b) by 1078 days.

(21) Appl. No.: 13/700,175

(22) PCT Filed: May 27, 2011

(86) PCT No.: PCT/DE2011/001150
§ 371 (c)(1),
(2), (4) Date: Nov. 27, 2012

(87) PCT Pub. No.: WO2011/147407
PCT Pub. Date: Dec. 1, 2011

(65) Prior Publication Data
US 2013/0123695 A1 May 16, 2013

(30) Foreign Application Priority Data
May 27, 2010 (DE) .................. 102010022588.6

(51) Int. Cl.
| A61L 29/16 | (2006.01) |
| A61L 29/08 | (2006.01) |
| A61K 31/337 | (2006.01) |
| A61K 31/436 | (2006.01) |

(52) U.S. Cl.
CPC ............ *A61L 29/16* (2013.01); *A61K 31/337* (2013.01); *A61K 31/436* (2013.01); *A61L 29/08* (2013.01); *A61L 29/085* (2013.01)

(58) Field of Classification Search
None
See application file for complete search history.

(56) References Cited

U.S. PATENT DOCUMENTS

| 4,110,470 A * | 8/1978 | Kummer ............ C07D 233/78 514/538 |
| 5,102,402 A | 4/1992 | Dror et al. |
| 6,761,731 B2 * | 7/2004 | Majercak ................ A61F 2/91 604/103.07 |
| 8,597,720 B2 * | 12/2013 | Hoffmann ............... A61L 29/16 118/258 |
| 2005/0033413 A1 * | 2/2005 | Fleming, III ............ A61F 2/91 623/1.15 |
| 2008/0118544 A1 | 5/2008 | Wang |
| 2008/0276935 A1 * | 11/2008 | Wang .................... A61K 31/337 128/203.15 |
| 2010/0055294 A1 * | 3/2010 | Wang .................... B05D 1/002 427/2.25 |
| 2010/0076542 A1 * | 3/2010 | Orlowski ............... A61L 29/10 623/1.12 |
| 2010/0179475 A1 * | 7/2010 | Hoffmann ............... A61L 29/16 604/103.02 |

FOREIGN PATENT DOCUMENTS

| EP | 0 383 429 A2 | 8/1990 |
| EP | 1 189 553 A1 | 3/2002 |
| EP | 2 092 942 A1 | 8/2009 |
| WO | 94/23787 A1 | 10/1994 |
| WO | 02/43796 A2 | 6/2002 |
| WO | 03/026718 A1 | 4/2003 |
| WO | 03/059430 A1 | 7/2003 |

OTHER PUBLICATIONS

International Search Report for PCT/DE2011/001150 dated Feb. 2, 2012.

* cited by examiner

*Primary Examiner* — Melissa S Mercier
(74) *Attorney, Agent, or Firm* — Thrive IP®; Georg Hasselmann

(57) ABSTRACT

The present invention relates to balloon catheters with or without crimped stent, whose surface is coated with at least one antirestenotic agent and at least one transport promoting molecular dispersant, as well as a method for the preparation of these medical devices.

6 Claims, No Drawings

BALLOON CATHETER COATED WITH AN ANTI-RESTENOTIC ACTIVE INGREDIENT AND A MOLECULAR DISPERSION AGENT THAT PROMOTES TRANSPORT

The present invention relates to medical devices short-term contacted with the organism, e.g. balloon catheter with or without crimped stent, whose surface is coated with at least one antirestenotic agent and a transport promoting molecular dispersant, and to methods for preparation of these medical devices and their use in prophylaxis or reduction of restenoses in a concerned body lumen.

STATE OF THE ART

After introducing short-term as well as long-term implants (stents or catheter balloons) into blood vessels reocclusion of vessels frequently occurs as a complication, which is known as restenosis. According to the relevant technical literature restenosis can be defined as a reduction of the vessel diameter to less than 50%, wherein this is an empirical determination.

The stents being implanted for treatment of stenoses and prophylaxis or reduction of restenoses, or the catheter balloons being used for dilations of the vessel evoke inflammatory reactions, which play an important role for the healing process in the first 7 days. The occurring processes are interrelated among others with the distribution of growth factors, whereby an increased proliferation of smooth muscle cells is initiated, and so lead already in a short-term to a restenosis and a new reocclusion of vessels due to uncontrolled growth.

Drug eluting catheter balloons offer an alternative to conventional stent coated with agent (CardioNews Letter Apr. 21, 2006). The problem of conventional catheter balloons coated with agent and possibly a polymeric matrix however is a sufficiently tight binding of the agent to the balloon surface during insertion of the cartheter balloon in order to prevent a premature washing off in the bloodstream and to ensure the adequate delivery of the agent from the balloon surface to the vessel wall during the dilatation within a few minutes or only one minute in order to effectively prevent restenosis or reduce it.

A major problem in the embodiments of the prior art, however, is that not sufficient antirestenotic agent can be transmitted to the affected vessel section during the dilation time of at most one minute and during possibly several repetitions of the dilatation, such that restenosis is not effectively prevented even upon dilatation of a catheter balloon without crimped stent. Since heart attack risk increases especially when used in coronary arteries upon extended dilation, there remains in total only little time for the transfer of the agent or agents to the vessel wall. Other problems of the prior art are low transmission amounts of the agent or agents into the vessel wall, no control over the dosage, problems with the balloon material, etc. Another problem is the transport of the agent to the targeting site, since parts of the coating can be detached during insertion and guidance of the balloon catheter in the bloodstream to the targeting site and thus an unknown amount of agent can reach the affected area. Thus, the efficiency of such a coated catheter balloon for antirestenotic treatment is individual and uncontrolled.

It is the objective of the present invention to provide a coating system that reduces effectively the premature release of agents from the surface of the catheter balloons and ensures the drug delivery from the balloon surface on the vessel wall in a shorter period than a minute with the most highly effective form.

This objective is solved by the technical teaching of the independent claims of the present invention. Further advantageous embodiments of the invention reside from the dependent claims, the description and the examples.

DESCRIPTION OF THE INVENTION

Surprisingly it was found that a combination of an anti-restenotic agent and a transport promoting molecular dispersant, which is not polymer, solves this objective best possible.

Thus, the present invention relates to a catheter balloon with or without crimped stent, wherein the surface of the catheter balloon is coated at least partially with at least one antirestenotic agent and at least one transport promoting molecular dispersant.

The present invention thus relates to catheter balloons with or without crimped stent, with a coating of an antirestenotic agent and a transport promoting molecular dispersant, wherein the coating combination ensures a sufficient adhesion and decomposition stability of the active agent and shows high release kinetics.

The invention is advantageous, because no or very little amount of agent is lost in the bloodstream and thereby the amount of agent can exactly be determined at the targeting site. Further, even at short contact time of the catheter balloon with the vessel wall a controllable and optimal agent delivery from the surface of the catheter balloon to the vessel wall is ensured. In addition, the agent in the transport promoting molecular dispersant is in such a form, which prevents the formation of particles or crystals and in particular larger particles or crystals, because particles and crystals, and in particular particles and crystals show no longer an antirestenotic effect and only increase the amount of applied agent, without achieving a measurable therapeutic effect. Thus, fine or molecular dispersed agent in the transport promoting molecular dispersant is preferred, because then only active agent molecules are delivered to the vessel wall upon the dilation and the transport promoting molecular dispersant in addition provides a good transfer of the agent on the vessel wall during the very short dilatation time of about 1 minute.

The present invention thus relates to catheter balloons having an agent eluting coating. The term catheter balloon or conventional catheter balloon as used in the present application refers to catheter balloons, bifurcation balloons, fold balloons, angioplasty balloons, PTCA balloons as well as special balloons such as slot balloons or needle balloons.

Here, the term "conventional catheter balloons" denotes dilatable catheter balloons that are used to dilate a vessel, particularly a blood vessel by means of dilatation and optionally set a stent simultaneously. Also non-dilatable catheter balloons for stent placement fall under the term, which are suitable for self-expanding stents and have a removable protective sheath over the stent to prevent premature expansion of stent.

Expandable and recompressible catheter balloons with a protective sheath such as non-dilatable balloon catheters for self-expanding stents, however are generally applied without a stent in order to protect the coating located on the catheter balloon from premature detachment.

Bifurcation balloons refer to catheter balloons for the treatment of a branch of a vessel in particular a blood vessel. Such balloons can have two arms, or consist of two connected or two separate balloons, which are applied simultaneously or successively for the treatment of a vessel bifurcation or for placement of a stent or two stents in a vessel bifurcation or in close vicinity to a vessel bifurcation.

Balloons are referred to as "fold balloons", as such balloons are described for example in EP 1189553 B1, U.S. Pat. No. 5,102,402, WO 03/059430 A1 and WO 94/23787 A1, and which have "folds" in the compressed state of the balloon, which open at least partially during the expansion of the balloon.

Balloons with pores are referred to as special balloons, in particular with micropores which allow the passage of liquids and solutions upon the expansion or upon the application of pressure. Such a balloon with microopenings is disclosed in EP 0383429A. Further, the term "special balloons" refers to balloons with specially designed surface such as the catheter balloon described in WO 02/043796 A2 with micro needles or the catheter balloon disclosed in WO 03/026718 A1 with a microrough or nanorough surface for storage of agents with or without carriers.

The term "balloon" or "catheter balloon" refers in principle to any expandable and recompressible as well as temporarily implantable medical device, which is usually used together with a catheter.

The coated balloons according to the present invention can be used without stent as well as with crimped stent. Their use is here not limited to initial treatment of stenotic vessels, but extends within the scope of the invention particularly to fight an occurring restenosis (e.g. in-stent restenosis) successfully and to prevent repeated constriction.

The catheter balloon can consist of the common materials, particularly polymers, as described further below and in particular of polyamide, such as PA 12, polyester, polyurethane, polyacrylates, polyethers, etc.

The stent can also consist of the common materials, such as surgical stainless steel, titanium, chromium, vanadium, tungsten, molybdenum, gold, nitinol, magnesium, iron, alloys of the aforementioned metals as well as of polymeric material and preferably absorbable polymeric material such as chitosan, heparans, polyhydroxybutyrate (PHB), polyglycerides, polylactides and copolymers of the aforementioned substances.

Preferably, the coated catheter balloons according to the present invention are used without crimped stent; however, a use with crimped stent is also possible and preferred. If a crimped stent is used besides the coated balloon, then the stent may be uncoated (bare stent) or may also be coated, wherein the stent can have a different coating and also a different agent than the coating of the catheter balloon.

The term "coating" should comprise not only a coating of the surface of the catheter balloon but also a filling or coating of folds, cavities, pores, microneedles or other Tillable areas on or between or within the balloon material.

Agents refer to substances which have a pharmacological activity. Antirestenotic agents comprise substances that inhibit the proliferation of smooth muscle cells that would otherwise lead to the reocclusion of an extended vessel. Preferred antirestenotic agents according to the present invention include paclitaxel, docetaxel, rapamycin (sirolimus), biolimus A9, zotarolimus, everolimus, myolimus, novolimus, pimecrolimus, tacrolimus, ridaforolimus and temsirolimus. The use of paclitaxel is thereby particularly preferred. Further preferred is the use of sirolimus or sirolimus combined with paclitaxel.

In principle, any agents and agent combinations can be used. However combinations of paclitaxel or sirolimus with other agents are preferred.

As solvents are used volatile organic compounds such as dichloromethane, chloroform, ethanol, acetone, heptane, n-hexane, DMF, DMSO, methanol, propanol, tetrahydrofuran (THF), methylene chloride, methyl acetate, ethyl acetate, ether, petroleum ether, acetonitrile, acetic acid ethyl and methyl ester, cyclohexane, and corresponding mixtures. Depending on the coating material (e.g. hydrogels or water soluble agents) the presence of water can also be desirable. Particularly preferred are acetone, ethanol and ethyl acetate. Depending on agent and transport promoting molecular dispersant also polar solvents, such as glycerol, ethylene glycol or water can be used.

Molecular dispersants are in the meaning of the invention substances which form a mixture with at least one antirestenotic agent without chemically reacting with each other. Furthermore, the antirestenotic agent should exist finely dispersed in the transport promoting molecular dispersant up to molecular and with particle sizes <1 nm. This inventive coating is advantageous because the agent or agents are dispersed finely and preferably homogeneously with the transport promoting molecular dispersant and are not released prematurely from the catheter balloon into the blood stream. Thus, in a preferred embodiment of the present invention, the at least one agent is embedded in the at least one transport promoting molecular dispersant or stored preferably in molecular form or in particle form having an average particle size of less than 1 nm.

According to the present invention substances are called transport promoting, which increase the transfer of at least one agent from the surface of the catheter balloon to or into the cells and/or the tissue of the vessel wall as compared to a transfer of the same agent without transport promoter. Thus, transport promoting are substances that accelerate and facilitate the absorption of agents into the vessel wall or the transfer of agents on the vessel wall, such that the existing agent or agent combination can be controlled during the short-term contact and transferred with the prescribed dosage to the vessel wall.

Compared to the prior art the at least one agent is transferred within a time span of a few minutes, preferably one minute, more preferably 50 seconds, even more preferably 40 seconds and particularly preferably 30 seconds from the balloon surface to the cell wall. Also for that reason the feature to transfer within a short time a maximum portion of the at least one agent to the vessel wall is advantageous, because the risk of a heart attack is reduced by the short-term contact of the catheter balloon with the vessel wall and especially in coronary arteries by only short-term occlusion of the vessel. Also the short dilatation time reduces the risk of microfissures in the vessels.

According to the invention the transport promoting molecular dispersant serves to keep the at least one agent during the introducing of catheter balloon on its surface and to ensure the optimal transfer of the at least one agent at the targeting site during the dilatation of catheter balloon.

According to the invention it is particularly preferred that the amount ratio of the at least one antirestenotic agent and the at least one transport promoting molecular dispersant is from 95 wt % antirestenotic agent to 5 wt % transport promoting molecular dispersant to 5 wt % antirestenotic agent to 95 wt % transport promoting molecular dispersant. In a preferred embodiment, the amount ratio of the at least one antirestenotic agent and the at least one transport promoting molecular dispersing agent is from 90 wt % antirestenotic agent to 10 wt % transport promoting molecular dispersant to 10 wt % antirestenotic agent to 90 wt % transport promoting molecular dispersant. More preferable is an amount ratio of one antirestenotic agent and one transport promoting molecular dispersing agent from 95 wt % antirestenotic agent to 5 wt % transport promoting molecular dispersant to 70 wt % antirestenotic agent to 30 wt % transport promoting molecular dispersant.

According to the invention compounds of the following general formula (I) are used as transport promoting molecular dispersants:

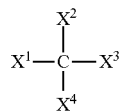

wherein
$X^1$ represents one of the following residues
-$L^1$-$R^{18}$, —C($R^3$)($R^4$)-$L^1$-$R^{18}$, -$L^1$-C($R^3$)($R^4$)—$R^{18}$, —C($R^3$)($R^4$)-$L^1$-C($R^5$)($R^6$)—$R^{18}$, -$L^1$-Y—$R^{13}$, —Y-$L^1$-$R^{18}$, —Y—C($R^3$)($R^4$)-$L^1$-$R^{18}$, —C($R^3$)($R^4$)—Y-$L^1$-$R^{18}$, —C($R^3$)($R^4$)-$L^1$-Y—$R^{18}$, —Y-$L^1$-C($R^3$)($R^4$)—$R^{18}$, -$L^1$-Y—C($R^3$)($R^4$)—$R^{18}$, -$L^1$-C($R^3$)($R^4$)—Y—$R^{18}$, —Y—C($R^3$)($R^4$)-$L^1$-C($R^5$)($R^6$)—$R^{18}$, —C($R^3$)($R^4$)—Y-$L^1$-C($R^5$)($R^6$)—$R^{18}$, —C($R^3$)($R^4$)-$L^1$-Y—C($R^5$)($R^6$)—$R^{18}$, —C($R^3$)($R^4$)-$L^1$-C($R^5$)($R^6$)—Y—$R^{18}$;

$X^2$ represents one of the following residues —$R^7$, (—$CH_2$—)$_p$—$R^7$, (—O—$CH_2$—)$_p$—$R^7$;

$X^3$ represents one of the following residues
-$M^1$-$R^{26}$, -$M^1$-$M^2$-$R^{26}$, -$M^1$-($M^2$)$_r$-$M^3$-$R^{26}$, -$M^1$-($M^2$)$_r$-$M^3$-($M^4$)$_s$-$R^{26}$;

$X^4$ represents one of the following residues
-$L^2$-$R^{19}$, —C($R^{10}$)($R^{11}$)-$L^2$-$R^{19}$, -$L^2$-C($R^{10}$)($R^{11}$)—$R^{19}$, —C($R^{10}$)($R^{11}$)—C($R^{12}$)($R^{13}$)-$L^2$-$R^{19}$, —C($R^{10}$)($R^{11}$)-$L^2$-C($R^{12}$)($R^{13}$)—$R^{19}$, -$L^2$-C($R^{10}$)($R^{11}$)—C($R^{12}$)($R^{13}$)—$R^{19}$;

$L^1$ represents one of the following groups

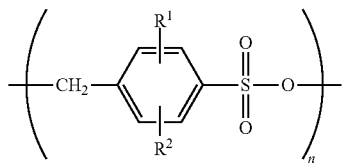

linker 1

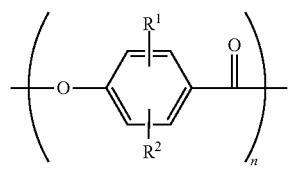

linker 2

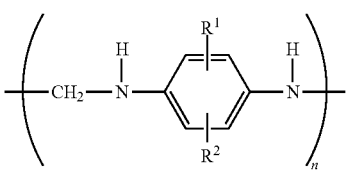

linker 3

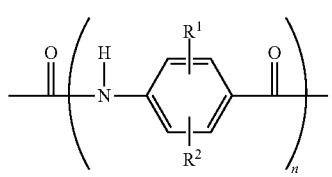

linker 4

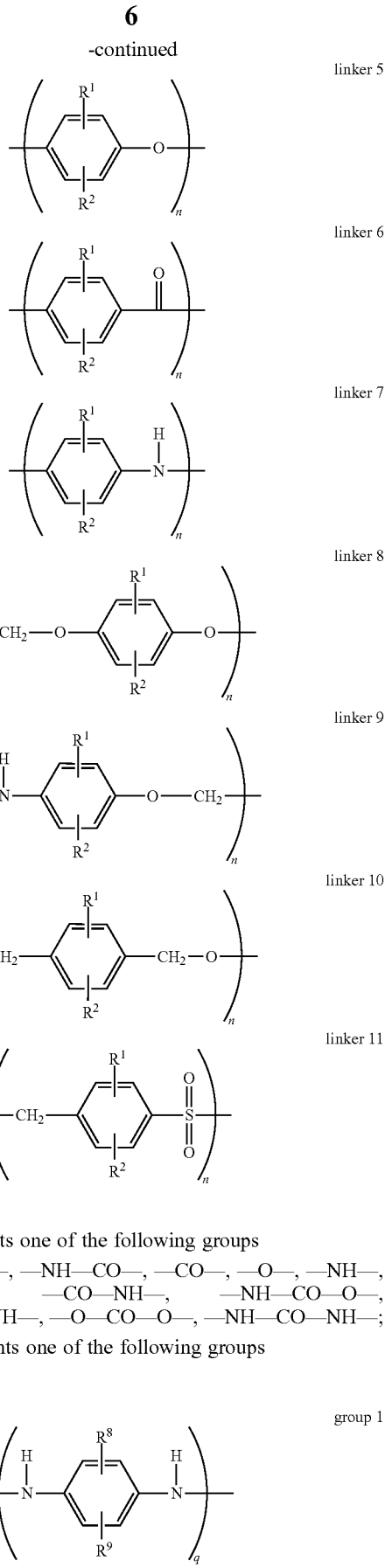

$L^2$ represents one of the following groups
—O—CO—, —NH—CO—, —CO—, —O—, —NH—, —CO—O—, —CO—NH—, —NH—CO—O—, —O—CO—NH—, —O—CO—O—, —NH—CO—NH—;

$M^1$ represents one of the following groups

-continued group 2

—N(H)—(CH₂)₆—N(H)— group 3

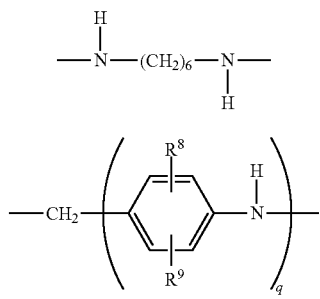

M² represents one of the following groups
—CH₂—, —CH₂—CH₂—, —CH₂—CH₂—CH₂—, —CH₂—CH₂—CH₂—CH₂—, —O—, —O—CH₂—, —O—CH₂—CH₂—, —O—CH₂—CH₂—CH₂—, —O—CH₂—CH₂—CH₂—CH₂—, —O—CO—, —O—CO—CH₂—, —O—CO—CH₂—CH₂—, —O—CO—CH₂—CH₂—CH₂—, —O—CO—CH₂—CH₂—CH₂—CH₂—, —CO—, —CO—CH₂—, —CO—CH₂—CH₂—, —CO—CH₂—CH₂—CH₂—, —CO—CH₂—CH₂—CH₂—CH₂—;

M³ represents one of the following groups
a bond, —NH—, —NH—CO—, —NH—CO—NH—, —NH—CS—, —NH—CS—NH—, —NH—C(NH)—NH—;

M⁴ represents one of the following groups
(—CH₂—O—CH₂—)$_t$, (—O—CH₂—CH₂—)$_t$, (—CH₂—CH₂—O—)$_t$;

Y represents (—CH₂—)$_m$, (—CH₂—O—)$_m$, (—O—CH₂—)$_m$, (—CH₂—CH₂—O—)$_m$ or (—CH₂—CH₂—CH₂—O—)$_m$;

$R^1$ to $R^{13}$ represent independently of each other the following residues:

—$R^{14}$ to —$R^{30}$, —OH, —OCH₃, —OC₂H₅, —OC₃H₇, —O-cyclo-C₃H₅, —OCH(CH₃)₂, —OC(CH₃)₃, —OC₄H₉, —OPh, —OCH₂-Ph, —OCPh₃, —SH, —SCH₃, —SC₂H₅, —SC₃H₇, —S-cyclo-C₃H₅, —SCH(CH₃)₂, —SC(CH₃)₃, —NO₂, —F, —Cl, —Br, —I, —P(O)(OH)₂, —P(O)(OCH₃)₂, —P(O)(OC₂H₅)₂, —P(O)(OCH(CH₃)₂)₂, —C(OH)[P(O)(OH)₂]₂, —Si(CH₃)₂(C(CH₃)₃), —Si(C₂H₅)₃, —Si(CH₃)₃, —N₃, —CN, —OCN, —NCO, —SCN, —NCS, —CHO, —COCH₃, —COC₂H₅, —COC₃H₇, —CO-cyclo-C₃H₅, —COCH(CH₃)₂, —COC(CH₃)₃, —COOH, —COCN, —COOCH₃, —COOC₂H₅, —COOC₃H₇, —COO-cyclo-C₃H₅, —COOCH(CH₃)₂, —COOC(CH₃)₃, —O—CO—R¹⁴, —CONH₂, —CONHCH₃, —CONHC₂H₅, —CONHC₃H₇, —CONH-cyclo-C₃H₅, —CONH[CH(CH₃)₂], —CONH[C(CH₃)₃], —CON(CH₃)₂, —CON(C₂H₅)₂, —CON(C₃H₇)₂, —CON(cyclo-C₃H₅)₂, —CON[CH(CH₃)₂]₂, —CON[C(CH₃)₃]₂, —NHCOCH₃, —NHCOC₂H₅, —NHCOC₃H₇, —NHCO-cyclo-C₃H₅, —NHCO—CH(CH₃)₂, —NHCO—C(CH₃)₃, —NHCO—OCH₃, —NHCO—OC₂H₅, —NHCO—OC₃H₇, —NHCO—O-cyclo-C₃H₅, —NHCO—OCH(CH₃)₂, —NHCO—OC(CH₃)₃, —NH₂, —NHCH₃, —NHC₂H₅, —NHC₃H₇, —NH-cyclo-C₃H₅, —NHCH(CH₃)₂, —NHC(CH₃)₃, —N(CH₃)₂, —N(C₂H₅)₂, —N(C₃H₇)₂, —N(cyclo-C₃H₅)₂, —N[CH(CH₃)₂]₂, —N[C(CH₃)₃]₂, —SOCH₃, —SOC₂H₅, —SOC₃H₇, —SO-cyclo-C₃H₅, —SOCH(CH₃)₂, —SOC(CH₃)₃, —SO₂CH₃, —SO₂C₂H₅, —SO₂C₃H₇, —SO₂-cyclo-C₃H₅, —SO₂CH(CH₃)₂, —SO₂C(CH₃)₃, —SO₃H, —SO₃CH₃, —SO₃C₂H₅, —SO₃C₃H₇, —SO₃-cyclo-C₃H₅, —SO₃CH(CH₃)₂, —SO₃C(CH₃)₃, —SO₂NH₂, —OCF₃, —OC₂F₅, —O—COOCH₃, —O—COOC₂H₅, —O—COOC₃H₇, —O—COO-cyclo-C₃H₅, —O—COOCH(CH₃)₂, —O—COOC(CH₃)₃, —NH—CO—NH₂, —NH—CO—NHCH₃, —NH—CO—NHC₂H₅, —NH—CO—NHC₃H₇, —NH—CO—NH-cyclo-C₃H₅, —NH—CO—NH[CH(CH₃)₂], —NH—CO—NH[C(CH₃)₃], —NH—CO—N(CH₃)₂, —NH—CO—N(C₂H₅)₂, —NH—CO—N(C₃H₇)₂, —NH—CO—N(cyclo-C₃H₅)₂, —NH—CO—N[CH(CH₃)₂]₂, —NH—CO—N[C(CH₃)₃]₂, —NH—CS—NH₂, —NH—CS—NHCH₃, —NH—CS—NHC₂H₅, —NH—CS—NHC₃H₇, —NH—CS—NH-cyclo-C₃H₅, —NH—CS—NH[CH(CH₃)₂], —NH—CS—NH[C(CH₃)₃], —NH—CS—N(CH₃)₂, —NH—CS—N(C₂H₅)₂, —NH—CS—N(C₃H₇)₂, —NH—CS—N(cyclo-C₃H₅)₂, —NH—CS—N[CH(CH₃)₂]₂, —NH—CS—N[C(CH₃)₃]₂, —NH—C(=NH)—NH₂, —NH—C(=NH)—NHCH₃, —NH—C(=NH)—NHC₂H₅, —NH—C(=NH)—NHC₃H₇, —NH—C(=NH)—NH-cyclo-C₃H₅, —NH—C(=NH)—NH[CH(CH₃)₂], —NH—C(=NH)—NH[C(CH₃)₃], —NH—C(=NH)—N(CH₃)₂, —NH—C(=NH)—N(C₂H₅)₂, —NH—C(=NH)—N(C₃H₇)₂, —NH—C(=NH)—N(cyclo-C₃H₅)₂, —NH—C(=NH)—N[CH(CH₃)₂]₂, —NH—C(=NH)—N[C(CH₃)₃]₂, —O—CO—NH₂, —O—CO—NHCH₃, —O—CO—NHC₂H₅, —O—CO—NHC₃H₇, —O—CO—NH-cyclo-C₃H₅, —O—CO—NH[CH(CH₃)₂], —O—CO—NH[C(CH₃)₃], —O—CO—N(CH₃)₂, —O—CO—N(C₂H₅)₂, —O—CO—N(C₃H₇)₂, —O—CO—N(cyclo-C₃H₅)₂, —O—CO—N[CH(CH₃)₂]₂, —O—CO—N[C(CH₃)₃]₂, —O—CO—OCH₃, —O—CO—OC₂H₅, —O—CO—OC₃H₇, —O—CO—O-cyclo-C₃H₅, —O—CO—OCH(CH₃)₂, —O—CO—OC(CH₃)₃;

$R^{14}$ to $R^{30}$ represent independently of each other the following residues:
—CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, cyclo-C₃H₅, cyclo-C₄H₇, cyclo-C₅H₉, cyclo-C₆H₁₁, cyclo-C₇H₁₃, cyclo-C₈H₁₅, -Ph, —CH₂-Ph, —CPh₃, —H, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₇H₁₅, —C₈H₁₇, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, (CH₃)—C(CH₃)₃, —CH=CH₂, —CH₂—CH=CH₂, —C(CH₃)=CH₂, —CH=CH—CH₃, —C₂H₄—CH=CH₂, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—C₂H₅, —CH=CH—C₃H₇, —CH₂—CH=CH—CH=CH₂, —CH=CH—CH=CH—CH₃, —CH=CH—CH₂—CH=CH₂, —C(CH₃)=CH—CH=CH₂, —CH=C(CH₃)—CH=CH₂, —CH=CH—C(CH₃)=CH₂, —CH=CH—CH=CH—CH₃, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=C(CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, $—C(CH_3)=CH—CH=CH_2$, $—CH=C(CH_3)—CH=CH_2$, $—CH=CH—C(CH_3)=CH_2$, $—C_4H_8—CH=CH_2$, $—C_3H_6—CH=CH—CH_3$, $—C_2H_4—CH=CH—C_2H_5$, $—CH_2—CH=CH—C_3H_7$, $—CH=CH—C_4H_9$, $—C_3H_6—C(CH_3)=CH_2$, $—C_2H_4—CH(CH_3)—CH=CH_2$, $—CH_2—CH(CH_3)—CH_2—CH=CH_2$, $—CH(CH_3)—C_2H_4—CH=CH_2$, $—C_2H_4—CH=C(CH_3)_2$, $—C_2H_4—C(CH_3)=CH—CH_3$, $—CH_2—CH(CH_3)—CH=CH—CH_3$, $—CH(CH_3)—CH_2—CH=CH—CH_3$, $—CH_2—CH=CH—CH(CH_3)_2$, $—CH_2—CH=C(CH_3)—C_2H_5$, $—CH_2—C(CH_3)=CH—C_2H_5$, $—CH(CH_3)—CH=CH—C_2H_5$, $—CH=CH—CH_2—CH(CH_3)_2$, $—CH=CH—CH(CH_3)—C_2H_5$, $—CH=C(CH_3)—C_3H_7$, $—C(CH_3)=CH—C_3H_7$, $—CH_2—CH(CH_3)—C(CH_3)=CH_2$, $—CH(CH_3)—CH_2—C(CH_3)=CH_2$, $—CH(CH_3)—CH(CH_3)—CH=CH_2$, $—CH_2—C(CH_3)_2—CH=CH_2$, $—C(CH_3)_2—CH_2—CH=CH_2$, $—CH_2—C(CH_3)=C(CH_3)_2$, $—CH(CH_3)—CH=C(CH_3)_2$, $—C(CH_3)_2—CH=CH—CH_3$, $—CH(CH_3)—C(CH_3)=CH—CH_3$, $—CH=C(CH_3)—CH(CH_3)_2$, $—C(CH_3)=CH—CH(CH_3)_2$, $—C(CH_3)=C(CH_3)—C_2H_5$, $—CH=CH—C(CH_3)_3$, $—C(CH_3)_2—C(CH_3)=CH_2$, $—CH(C_2H_5)—C(CH_3)=CH_2$, $—C(CH_3)(C_2H_5)—CH=CH_2$, $—CH(CH_3)—C(C_2H_5)=CH_2$, $—CH_2—C(C_3H_7)=CH_2$, $—CH_2—C(C_2H_5)=CH—CH_3$, $—CH(C_2H_5)—CH=CH—CH_3$, $—C(C_4H_9)=CH_2$, $—C(C_3H_7)=CH—CH_3$, $—C(C_2H_5)=CH—C_2H_5$, $—C(C_2H_5)=C(CH_3)_2$, $—C[C(CH_3)_3]=CH_2$, $—C[CH(CH_3)(C_2H_5)]=CH_2$, $—C[CH_2—CH(CH_3)_2]=CH_2$, $—C_2H_4—CH=CH—CH=CH_2$, $—CH_2—CH=CH—CH_2—CH=CH_2$, $—CH=CH—C_2H_4—CH=CH_2$, $—CH_2—CH=CH—CH=CH—CH_3$, $—CH=CH—CH_2—CH=CH—CH_3$, $—CH=CH—CH=CH—C_2H_5$, $—CH_2—CH=CH—C(CH_3)=CH_2$, $—CH_2—CH=C(CH_3)—CH=CH_2$, $—CH_2—C(CH_3)=CH—CH=CH_2$, $—CH(CH_3)—CH=CH—CH=CH_2$, $—CH=CH—CH_2—C(CH_3)=CH_2$, $—CH=CH—CH(CH_3)—CH=CH_2$, $—CH=C(CH_3)—CH_2—CH=CH_2$, $—C(CH_3)=CH—CH_2—CH=CH_2$, $—CH=CH—CH=C(CH_3)_2$, $—CH=CH—C(CH_3)=CH—CH_3$, $—CH=C(CH_3)—CH=CH—CH_3$, $—C(CH_3)=CH—CH=CH—CH_3$, $—CH=C(CH_3)—C(CH_3)=CH_2$, $—C(CH_3)=CH—C(CH_3)=CH_2$, $—C(CH_3)=C(CH_3)—CH=CH_2$, $—CH=CH—CH=CH—CH=CH_2$, $—C≡CH$, $—C≡C—CH_3$, $—CH_2—C≡CH$, $—C_2H_4—C≡CH$, $—CH_2—C≡C—CH_3$, $—C≡C—C_2H_5$, $—C_3H_6—C≡CH$, $—C_2H_4—C≡C—CH_3$, $—CH_2—C≡C—C_2H_5$, $—C≡C—C_3H_7$, $—CH(CH_3)—C≡CH$, $—CH_2—CH(CH_3)—C≡CH$, $—CH(CH_3)—CH_2—C≡CH$, $—CH(CH_3)—C≡C—CH_3$, $—C_4H_8—C≡CH$, $—C_3H_6—C≡C—CH_3$, $—C_2H_4—C≡C—C_2H_5$, $—CH_2—C≡C—C_3H_7$, $—C≡C—C_4H_9$, $—C_2H_4—CH(CH_3)—C≡CH$, $—CH_2—CH(CH_3)—CH_2—C≡CH$, $—CH(CH_3)—C_2H_4—C≡CH$, $—CH_2—CH(CH_3)—C≡C—CH_3$, $—CH(CH_3)—CH_2—C≡C—CH_3$, $—CH(CH_3)—C≡C—C_2H_5$, $—CH_2—C≡C—CH(CH_3)_2$, $—C≡C—CH(CH_3)—C_2H_5$, $—C≡C—CH_2—CH(CH_3)_2$, $—C≡C—C(CH_3)_3$, $—CH(C_2H_5)—C≡C—CH_3$, $—C(CH_3)_2—C≡C—CH_3$, $—CH(C_2H_5)—CH_2—C≡CH$, $—CH_2—CH(C_2H_5)—C≡CH$, $—C(CH_3)_2—CH_2—C≡CH$, $—CH_2—C(CH_3)_2—C≡CH$, $—CH(CH_3)—CH(CH_3)—C≡CH$, $—CH(C_3H_7)—C≡CH$, $—C(CH_3)(C_2H_5)—C≡CH$, $—C≡C—C≡CH$, $—CH_2—C≡C—C≡CH$, $—C≡C—C≡C—CH_3$, $—CH(C≡CH)_2$, $—C_2H_4—C≡C—C≡CH$, $—CH_2—C≡C—CH_2—C≡CH$, $—C≡C—C_2H_4—C≡CH$, $—CH_2—C≡C—C≡C—CH_3$, $—C≡C—CH_2—C≡C—CH_3$, $—C≡C—C≡C—C_2H_5$, $—C≡C—CH(CH_3)—C≡CH$, $—CH(CH_3)—C≡C—C≡CH$, $—CH(C≡CH)—CH_2—C≡CH$, $—C(C≡CH)_2—CH_3$, $—CH_2—CH(C≡CH)_2$, $—CH(C≡CH)—C≡C—CH_3$;

m is an integer from 1 to 10;
n is an integer from 0 to 5;
p is an integer from 0 to 3;
q is an integer from 0 to 4;
r represents 0 or 1;
s represents 0 or 1;
t is an integer from 1 to 10

The transport promoting molecular dispersant for embedding of the at least one antirestenotic agent is thereby defined by means of concrete physical properties.

The transport promoting molecular dispersants are organic compounds containing carbon, hydrogen and oxygen, and optionally nitrogen. If the transport promoting molecular dispersants contain nitrogen, then the nitrogen is preferably present in amide bonds or in the form of an amine group. Such compounds contain preferably 1 to 5 amide bonds, more preferably 2 to 3 amide bonds and/or have 1 to 5 amine groups, wherein the total number of nitrogen atoms ranges from 1 to 10, preferably 2 to 7, more preferably from 3 to 5.

The nitrogen containing transport promoting molecular dispersants have melting points of above −20° C., preferably of above 0° C., more preferably of above 20° C. and particularly preferably of above 40° C., and boiling points of at least 470° C., preferably of at least 490° C., more preferably of at least 510° C., more preferably of at least 530° C., more preferably of at least 550° C., more preferably of at least 570° C., more preferably of at least 590° C., more preferably of at least 610° C. and particularly preferably a boiling point of at least 630° C. In addition, the boiling point should not exceed 650° C. The boiling points are valid for the normal pressure at sea level, i.e. 760 mm Hg.

A preferred subgroup are transport promoting molecular dispersants without nitrogen, which consist of carbon, hydrogen and oxygen and are not present as a salt and are not charged and bear no acidic proton. Such transport promoting molecular dispersants according to the general formula (I) preferably have a boiling point of at least 400° C., more preferably of at least 420° C., yet more preferably of at least 440° C., yet more preferably at least 460° C., yet more preferably of at least 470° C., yet more preferably of at least 480° C., yet more preferably of at least 490° C., and yet more preferably a boiling point of at least 500° C. In addition, the boiling point should not exceed 550° C. The boiling points are valid for the normal pressure (1.013 hPa) at sea level, i.e. 760 mm Hg.

The transport promoting molecular dispersants contain 1 to 15 oxygen atoms, more preferably 2 to 14, yet more preferably 3 to 13, yet more preferably 4 to 12, yet more preferably 5 to 11, yet more preferably 6 to 10, and particularly preferably 7 to 9 oxygen atoms. The oxygen atoms are preferably present in ester bonds or ether bonds. Furthermore, it is preferred there are in case of the presence of ether bonds from 4 to 12, more preferred from 5 to 11, further more preferred from 6 to 10 ether bonds, or in case of the presence of ester bonds 2 to 6, preferred 3 to 5 ester bonds.

The nitrogenfree transport promoting molecular dispersants according to general formula (I) have to have a molar mass (molecular weight) of at least 400 g/mol, more preferably of at least 420 g/mol, yet more preferably of at least 440 g/mol, yet more preferably at least 460 g/mol, yet more preferably from at least 470 g/mol, yet more preferably of at least 480 g/mol, yet more preferably of at least 490 g/mol and particularly preferably a molecular weight of at least 500 g/mol.

The nitrogen containing transport promoting molecular dispersants according to the general formula (I) have to have a molar mass (molecular weight) of at least 450 g/mol, more preferably of at least 460 g/mol, yet more preferably of at least 470 g/mol, yet more preferably of at least 480 g/mol, yet more preferably of at least 490 g/mol, yet more preferably of at least 500 g/mol, yet more preferably of at least 510 g/mol and particularly preferably a molecular weight of at least 520 g/mol.

In addition, the transport promoting molecular dispersants with at least one amino group or amide group have between 25 to 50 carbon atoms, preferably between 27 to 48 carbon atoms, more preferably between 29 to 46 carbon atoms, further preferably between 31 to 44 carbon atoms and particularly preferably between 33 to 42 carbon atoms, wherein the nitrogen free transport promoting molecular dispersants have between 20 to 40 carbon atoms, preferably between 22 to 38 carbon atoms, more preferably between 24 to 36 carbon atoms, more preferably between 26 to 34 carbon atoms and particularly preferably between 28 to 32 carbon atoms.

A preferred group of transport promoting molecular dispersants without nitrogen preferably has a melting point of above −80° C., more preferably of above −75° C., more preferably above of −70° C., more preferably above of −65° C. and particularly preferably a melting point of above −60° C. These melting points are particularly obtained by linear alkyl residues. Further, it has been found that the transport promoting molecular dispersants of the general formula (I) further should have a density of 0.80 g/cm$^3$ to 1.20 g/cm$^3$, more preferably from 0.85 g/cm$^3$ to 1.15 g/cm$^3$; more preferably 0.90 g/cm$^3$ to 1.10 g/cm$^3$, more preferably 0.93 g/cm$^3$ to 1.12 g/cm$^3$, and particularly preferably a density of 0.95 g/cm$^3$ to 1.05 g/cm$^3$.

Furthermore, it was found that the preferred transport promoting molecular dispersants of the general formula (I) have a flash point of above 50° C., more preferred of above 60° C., yet more preferred of above 70° C., yet more preferred of above 80° C., yet more preferred of above 85° C., yet more preferred of above 90° C., yet more preferred of above 95° C. and particularly preferred a flash point of above 100° C.

The measured refractive indices of the preferred transport promoting molecular dispersants according to general formula (I) were above 1.40 and below 1.50, so that a refractive index n20/D between 1.400 to 1.500 is preferred and more preferred a refractive index n20/D between 1.410 to 1.490, yet more preferred between 1.420 to 1.480, yet more preferred between 1.430 to 1.470, yet more preferred between 1.435 to 1.465, and particularly preferred is a refractive index n20/D between 1.440 to 1.460. It may be noted that such transport promoting molecular dispersants are the more preferred, the more the aforementioned chemical and physical parameters fall into the preferred ranges. Therefore best suited are such transport promoting molecular dispersants, which have all aforementioned parameters in the most preferred ranges.

A nitrogen containing transport promoting molecular dispersant having a refractive index n20/D of 1.49 and a boiling point of 480° C. and a density of 1.18 g/cm$^3$ is therefore less preferred than a nitrogen free transport promoting molecular dispersant having a refractive index n20/D of 1.44 and a boiling point of 510° C. and a density of 1.00 g/cm$^3$, as far as all other parameters of both compounds are outside the preferred ranges.

In addition, it may be mentioned that the determination of the refractive index, the boiling point, the melting point, flash point and the density is carried out by means of standard methods well known to the skilled person.

These 19 Transport promoting molecular dispersants described in Table 1 were tested as coating materials for catheter balloons together with an antirestenotic agent. These 19 compounds are either commercially available or accessible by simple syntheses and standard reactions such as esterification or preparation of amide bonds.

TABLE 1

| Residues/Compound | $X^1$ | $X^2$ | $X^3$ | $X^4$ |
|---|---|---|---|---|
| compd. 1 | —Y—L$^1$—R$^{18}$<br>Y = —CH$_2$—<br>L$^1$ = linker 5, (n = 1)<br>R$^1$ = R$^2$ = —H<br>R$^{18}$ = cyclo-C$_3$H$_5$ | —COO—C$_2$H$_5$ | —M$^1$—(M$^2$)$_r$—M$^3$—R$^{26}$<br>M$^1$ = group 1 (q = 0)<br>M$^2$ = —CH$_2$—, (r = 0)<br>M$^3$ = —NH—<br>R$^{26}$ = cyclo-C$_3$H$_5$ | —C(R$^{10}$)(R$^{11}$)—L$^2$—R$^{19}$<br>L$^2$ = —NH—CO—<br>R$^{10}$ = R$^{11}$ = —H<br>R$^{19}$ = —CH$_3$ |
| compd. 2 | —Y—L$^1$—C(R$^3$)(R$^4$)—R$^{18}$<br>Y = —C$_2$H$_4$—<br>L$^1$ = linker 2, (n = 1)<br>R$^1$ = R$^2$ = —H<br>R$^3$ = R$^4$ = —H<br>R$^{18}$ = —C$_5$H$_{11}$ | —OC$_3$H$_7$ | —M$^1$—(M$^2$)$_r$—M$^3$—(M$^4$)$_s$—R$^{26}$<br>M$^1$ = group 2 (q = 0)<br>M$^2$ = —O—, (r = 1);<br>M$^3$ = bond<br>M$^4$ = (—C$_2$H$_4$O—)$_5$, (s = 1);<br>R$^{26}$ = —C$_2$H$_5$ | —C(R$^{10}$)(R$^{11}$)—L$^2$—C(R$^{12}$)(R$^{13}$)—R$^{19}$<br>L$^2$ = —O—CO—<br>R$^{10}$ = R$^{11}$ = —H<br>R$^{12}$ = R$^{13}$ = —H<br>R$^{19}$ = —C$_4$H$_9$ |
| compd. 3 | —L$^1$—C(R$^3$)(R$^4$)—Y—R$^{18}$<br>Y = —CH$_2$O—CH$_2$O—<br>L$^1$ = linker 3, (n = 1)<br>R$^1$ = R$^2$ = —H<br>R$^3$ = R$^4$ = —H<br>R$^{18}$ = —CH$_3$ | —OCH$_2$—N(CH$_3$)$_2$ | —M$^1$—R$^{26}$<br>M$^1$ = group 1 (q = 1)<br>R$^8$ = R$^9$ = —H<br>R$^{26}$ = —C$_2$H$_5$ | —L$^2$—C(R$^{10}$)(R$^{11}$)—R$^{19}$<br>L$^2$ = —NH—CO—<br>R$^{10}$ = R$^{11}$ = —H<br>R$^{19}$ = —CH$_2$—CF$_3$ |
| compd. 4 | —C(R$^3$)(R$^4$)—L$^1$—Y—C(R$^5$)(R$^6$)—R$^{18}$<br>Y = —CH$_2$—<br>L$^1$ = linker 4, (n = 1)<br>R$^1$ = R$^2$ = —H<br>R$^3$ = R$^4$ = —H<br>R$^5$ = R$^6$ = —H<br>R$^{18}$ = —C≡C—CH$_3$ | —CONH$_2$ | —M$^1$—(M$^2$)$_r$—M$^3$—(M$^4$)$_s$—R$^{26}$<br>M$^1$ = group 3 (q = 0)<br>M$^2$ = —O—, (r = 1)<br>M$^3$ = —NH—CO—<br>M$^4$ = —OC$_2$H$_4$—, (s = 0)<br>R$^{26}$ = —C$_4$H$_9$ | —L$^2$—C(R$^{10}$)(R$^{11}$)—C(R$^{12}$)(R$^{13}$)—R$^{19}$<br>L$^2$ = —CO—NH—<br>R$^{10}$ = R$^{11}$ = —H<br>R$^{12}$ = R$^{13}$ = —H<br>R$^{19}$ = —C$_6$H$_{13}$ |
| compd. 5 | —L$^1$—Y—C(R$^3$)(R$^4$)—R$^{18}$<br>Y = —CH$_2$— | —COO-cyclo-C$_3$H$_5$ | —M$^1$—(M$^2$)$_r$—M$^3$—(M$^4$)$_s$—R$^{26}$<br>M$^1$ = group 2 (q = 0) | —C(R$^{10}$)(R$^{11}$)—C(R$^{12}$)(R$^{13}$)—L$^2$—R$^{19}$ |

TABLE 1-continued

| Residues/Compound | X¹ | X² | X³ | X⁴ |
|---|---|---|---|---|
| | $L^1$ = linker 5, (n = 1)<br>$R^1$ = $R^2$ = —H<br>$R^3$ = $R^4$ = —H<br>$R^{18}$ = —CH₃ | | $M^2$ = —CH₂—, (r = 1);<br>$M^3$ = —NH—CO—<br>$M^4$ = —C₂H₄O—, (s = 1);<br>$R^{26}$ = —CH₃ | $L^2$ = —COO—<br>$R^{10}$ = $R^{11}$ = —H<br>$R^{12}$ = $R^{13}$ = —H<br>$R^{19}$ = —C₄H₉ |
| compd. 6 | —C(R³)(R⁴)—L¹—R¹⁸<br>$L^1$ = linker 1, (n = 2)<br>$R^1$ = $R^2$ = —H<br>$R^3$ = $R^4$ = —H<br>$R^{18}$ = —CH₃ | —CO—OCH₃ | —M¹—R²⁶<br>$M^1$ = group 1 (q = 0)<br>$R^{26}$ = —C₄H₉ | —C(R¹⁰)(R¹¹)—L²—R¹⁹<br>$L^2$ = —CO—<br>$R^{10}$ = $R^{11}$ = —H<br>$R^{19}$ = —C₆H₁₃ |
| compd. 7 | —L¹—Y—R¹⁸<br>Y = (—CH₂CH₂O—)ₘ<br>m = 3<br>$L^1$ = linker 6, (n = 1)<br>$R^1$ = $R^2$ = —H<br>$R^{18}$ = —C₂H₅ | —OCH₂—OCH₃ | —M¹—R²⁶<br>$M^1$ = group 1 (q = 0)<br>$R^{26}$ = —C₆H₁₃ | —L²—C(R¹⁰)(R¹¹)—R¹⁹<br>$L^2$ = —O—<br>$R^{10}$ = $R^{11}$ = —H<br>$R^{19}$ = —C₄H₉ |
| compd. 8 | —C(R³)(R⁴)—L¹—C(R⁵)(R⁶)—R¹⁸<br>$L^1$ = linker 4, (n = 1)<br>$R^1$ = $R^2$ = —H<br>$R^3$ = $R^4$ = —H<br>$R^5$ = $R^6$ = —H<br>$R^{18}$ = —C₂H₅ | —N(Me)₂<br>Me = CH₃ | —M¹—(M²)ᵣ—M³—(M⁴)ₛ—R²⁶<br>$M^1$ = group 2 (q = 0)<br>$M^2$ = —COCH₂CH₂—, (r = 1);<br>$M^3$ = bond<br>$M^4$ = (—OC₂H₄—)₄, (s = 1);<br>$R^{26}$ = —H | —C(R¹⁰)(R¹¹)—L²—C(R¹²)(R¹³)—R¹⁹<br>$L^2$ = —O—CO—<br>$R^{10}$ = $R^{11}$ = —H<br>$R^{12}$ = $R^{13}$ = —H<br>$R^{19}$ = —CH₃ |
| compd. 9 | —L¹—C(R³)(R⁴)—R¹⁸<br>$L^1$ = linker 7, (n = 1)<br>$R^1$ = $R^2$ = —H<br>$R^3$ = $R^4$ = —H<br>$R^{18}$ = —C₆H₁₃ | —COOH | —M¹—(M²)ᵣ—M³—R²⁶<br>$M^1$ = group 1 (q = 0)<br>$M^2$ = —CH₂—, (r = 0)<br>$M^3$ = —NH—CO—<br>$R^{26}$ = —C₂H₅ | —L²—R¹⁹<br>$L^2$ = —NH—CO—O—<br>$R^{19}$ = cyclo-C₃H₅ |
| compd. 10 | —Y—C(R³)(R⁴)—L¹—R¹⁸<br>Y = (—CH₂O—)ₘ<br>m = 4<br>$L^1$ = linker 8, (n = 1)<br>$R^1$ = $R^2$ = —H<br>$R^3$ = $R^4$ = —H<br>$R^{18}$ = —CH₃ | —CH₂—OC₂H₅ | —M¹—(M²)ᵣ—M³—(M⁴)ₛ—R²⁶<br>$M^1$ = group 2 (q = 0)<br>$M^2$ = —CH₂—, (r = 0);<br>$M^3$ = —NH—CO—<br>$M^4$ = —C₂H₄O—, (s = 1);<br>$R^{26}$ = cyclo-C₅H₉ | —C(R¹⁰)(R¹¹)—L²—R¹⁹<br>$L^2$ = —CO—NH—<br>$R^{10}$ = $R^{11}$ = —H<br>$R^{19}$ = —C₅H₁₁ |
| compd. 11 | —C(R³)(R⁴)—Y—L¹—R¹⁸<br>Y = (—OCH₂—)ₘ<br>m = 2<br>$L^1$ = linker 5, (n = 1)<br>$R^1$ = $R^2$ = —H<br>$R^3$ = $R^4$ = —H<br>$R^{18}$ = —CH₃ | —OCH₂—OH | —M¹—(M²)ᵣ—M³—(M⁴)ₛ—R²⁶<br>$M^1$ = group 3 (q = 0)<br>$M^2$ = —COCH₂—, (r = 1)<br>$M^3$ = —NH—<br>$M^4$ = —OC₂H₄—, (s = 0)<br>$R^{26}$ = —C₄H₉ | —C(R¹⁰)(R¹¹)—C(R¹²)(R¹³)—L²—R¹⁹<br>$L^2$ = —CO—<br>$R^{10}$ = $R^{11}$ = —H<br>$R^{12}$ = $R^{13}$ = —H<br>$R^{19}$ = —CH₂—C≡CH |
| compd. 12 | —C(R³)(R⁴)—L¹—Y—R¹⁸<br>Y = (—CH₂CH₂O—)ₘ<br>m = 4<br>$L^1$ = linker 4, (n = 0)<br>$R^1$ = $R^2$ = —H<br>$R^3$ = $R^4$ = —H<br>$R^{18}$ = —CH₃ | —O—C(CH₃)₃ | —M¹—(M²)ᵣ—M³—(M⁴)ₛ—R²⁶<br>$M^1$ = group 1 (q = 0)<br>$M^2$ = —O—CO—CH₂—CH₂—CH₂—, (r = 1)<br>$M^3$ = bond<br>$M^4$ = —C₂H₄O—, (s = 1)<br>$R^{26}$ = —C₃H₇ | —L²—C(R¹⁰)(R¹¹)—C(R¹²)(R¹³)—R¹⁹<br>$L^2$ = —O—CO—<br>$R^{10}$ = $R^{11}$ = —H<br>$R^{12}$ = $R^{13}$ = —H<br>$R^{19}$ = —C₅H₁₁ |
| compd. 13 | —L¹—R¹⁸<br>$L^1$ = linker 2, (n = 3)<br>$R^1$ = $R^2$ = —H<br>$R^{18}$ = —C₄H₉ | —O—CO—C₃H₇ | —M¹—R²⁶<br>$M^1$ = group 1 (q = 0)<br>$R^{26}$ = —C₅H₁₁ | —L²—R¹⁹<br>$L^2$ = —O—CO—O—<br>$R^{19}$ = —C₃H₇ |
| compd. 14 | —Y—C(R³)(R⁴)—L¹—C(R⁵)(R⁶)—R¹⁸<br>Y = —CH₂O—<br>$L^1$ = linker11, (n = 1)<br>$R^1$ = $R^2$ = —H<br>$R^3$ = $R^4$ = —H<br>$R^5$ = $R^6$ = —H<br>$R^{18}$ = —OC₂H₅ | —CH₂—OC₂H₅ | —M¹—M²—R²⁶<br>$M^1$ = group 2 (q = 1)<br>$M^2$ = —CH₂—CH₂—<br>$R^{26}$ = —C₅H₁₁ | —C(R¹⁰)(R¹¹)—L²—C(R¹²)(R¹³)—R¹⁹<br>$L^2$ = —CO—<br>$R^{10}$ = $R^{11}$ = —H<br>$R^{12}$ = $R^{13}$ = —H<br>$R^{19}$ = —C₆H₁₃ |
| compd. 15 | —C(R³)(R⁴)—Y—L¹—C(R⁵)(R⁶)—R¹⁸<br>Y = —OCH₂—<br>$L^1$ = linker 2, (n = 1)<br>$R^1$ = $R^2$ = —H<br>$R^3$ = $R^4$ = —H<br>$R^5$ = $R^6$ = —H<br>$R^{18}$ = —CH(CH₃)₂ | —O-cyclo-C₃H₅ | —M¹—(M²)ᵣ—M³—R²⁶<br>$M^1$ = group 1 (q = 1)<br>$M^2$ = —CH₂—, (r = 1)<br>$M^3$ = —NH—CO—<br>$R^8$ = $R^9$ = —H<br>$R^{26}$ = —CH₃ | —L²—C(R¹⁰)(R¹¹)—R¹⁹<br>$L^2$ = —O—CO—<br>$R^{10}$ = $R^{11}$ = —H<br>$R^{19}$ = —H |
| compd. 16 | —C(R³)(R⁴)—L¹—C(R⁵)(R⁶)—Y—R¹⁸<br>Y = —CH₂—<br>$L^1$ = linker10, (n = 1)<br>$R^1$ = $R^2$ = —H<br>$R^3$ = $R^4$ = —H<br>$R^5$ = $R^6$ = —H<br>$R^{18}$ = —H | —O—CH(Me)₂<br>Me = CH₃ | —M¹—(M²)ᵣ—M³—(M⁴)ₛ—R²⁶<br>$M^1$ = group 1 (q = 0)<br>$M^2$ = —CH₂—, (r = 0)<br>$M^3$ = —NH—CO—<br>$M^4$ = —OC₂H₄—, (s = 0)<br>$R^{26}$ = —C₂H₅ | —L²—C(R¹⁰)(R¹¹)—C(R¹²)(R¹³)—R¹⁹<br>$L^2$ = —COO—<br>$R^{10}$ = $R^{11}$ = —H<br>$R^{12}$ = $R^{13}$ = —H<br>$R^{19}$ = —C₄H₉ |
| compd. 17 | —L¹—Y—R¹⁸<br>Y = —CH₂O— | —O—CO—OC₂H₅ | —M¹—(M²)ᵣ—M³—R²⁶<br>$M^1$ = group 2 (q = 1) | —L²—C(R¹⁰)(R¹¹)—R¹⁹<br>$L^2$ = —CO— |

TABLE 1-continued

| Residues/Compound | $X^1$ | $X^2$ | $X^3$ | $X^4$ |
|---|---|---|---|---|
| | $L^1$ = linker 5, (n = 1)<br>$R^1 = R^2 =$ —H<br>$R^{18} =$ —$C_3H_7$ | | $M^2 =$ —$CH_2CH_2CH_2$—, (r = 1)<br>$M^3 =$ —NH—<br>$R^{26} =$ —$C_2H_5$ | $R^{10} = R^{11} =$ —H<br>$R^{19} =$ —$CH(CH_3)_2$ |
| compd. 18 | —Y—$L^1$—$R^{18}$<br>Y = —$CH_2$—$CH_2$—<br>$L^1$ = linker 9, (n = 1)<br>$R^1 = R^2 =$ —H<br>$R^{18}$ = -cyclo-$C_3H_5$ | —$OC_2H_5$ | —$M^1$—$(M^2)_r$—$M^3$—$(M^4)_s$—$R^{26}$<br>$M^1$ = group 2 (q = 0)<br>$M^2 =$ —O—CO—$CH_2$—, (r = 1);<br>$M^3 =$ —NH—<br>$M^4 =$ —$OC_2H_4$—, (s = 0)<br>$R^{26} =$ —$C_6H_{13}$ | —$C(R^{10})(R^{11})$—$C(R^{12})$<br>$(R^{13})$—$L^2$—$R^{19}$<br>$L^2 =$ —CO—NH—<br>$R^{10} = R^{11} =$ —H<br>$R^{12} = R^{13} =$ —H<br>$R^{19} =$ —$C_2H_5$ |
| compd. 19 | —$L^1$—Y—$C(R^3)(R^4)$—$R^{18}$<br>Y = —$CH_2$—<br>$L^1$ = linker 7, (n = 1)<br>$R^1 = R^2 =$ —H<br>$R^3 = R^4 =$ —H<br>$R^{18} =$ —H | —CO—$OC_3H_7$ | —$M^1$—$M^2$—$R^{26}$<br>$M^1$ = group 3 (q = 1)<br>$M^2 =$ —CO—<br>$R^8 = R^9 =$ —H<br>$R^{26} =$ —$C_3H_7$ | —$L^2$—$R^{19}$<br>$L^2 =$ —O—CO—NH—<br>$R^{19} =$ —$C_6H_{13}$ |

For the full or partial coating of a catheter balloon with or without a crimped stent a solution consisting of the at least one antirestenotic agent and the at least one transport promoting molecular dispersant and the solvent or solvent mixture including potential additives is applied by spraying, dipping, brushing, injecting, drag, rolling or pipetting method or electrospinning on the catheter balloon surface. The catheter balloon can be coated partially or completely either in expanded or in folded state, or together with a crimped stent. These coating methods are state of the art and disclosed in detail in U.S. Pat. No. 8,597,720. Phosphatidylinositol, phosphatidylserine, phosphatidylcholine, phosphatidylethanolamine, phosphatidic acid or other phosphatidyl compounds can be used as optional additives in amounts up to 50 wt % based on all components of the coating.

The term "coating" is intended to comprise not only a coating of the surface of the catheter balloon but also a filling or coating of folds, cavities, pores, micro-needles or other fillable spaces on or between or within the balloon material.

The drying of the inventive coating on the balloon surface can be done, for example by leaving to air (evaporation of the solvent) or by heating and/or reduced pressure (vacuum) or rotary drying, which is described in detail in U.S. Pat. No. 8,597,720. Thereby the solvent is removed so that the coating consists of the at least one agent and the at least one transport promoting molecular dispersant.

The coating solution thus contains at least one agent, at least one transport promoting molecular dispersant, and at least one solvent.

The following examples describe the present invention without limiting the same to the specific embodiments.

EXAMPLES

Example 1: Coating a Catheter Balloon with Paclitaxel and Compound 1

An unexpanded catheter balloon is rotatably mounted on a horizontal rod. A solution of 90 wt % paclitaxel in ethanol and 10 wt % of compound 1 is applied by means of a spray device onto the catheter balloon surface. Subsequently, the catheter balloon is dried with slow rotation (20 rpm) at room temperature overnight.

Example 2: Coating a Catheter Balloon with Paclitaxel and Compound 2

A catheter balloon is rotatably mounted on a horizontal rod and coated by means of pipetting method with a solution of 85 wt % pacliltaxel in methanol and 15 wt % compound 2. Subsequently, the catheter balloon is dried with slow rotation at room temperature for several hours.

Example 3: Coating a Catheter Balloon with Paclitaxel and Compound 3

A catheter balloon is dipped in a solution of 80 wt % paclitaxel in acetone and 20 wt % compound 3 and subsequently dried with slow rotation about its longitudinal axis at room temperature. The dipping procedure is repeated 2 more times.

Example 4: Coating a Catheter Balloon with Paclitaxel and Compound 4

A catheter balloon is rotatably mounted on a horizontal rod and coated by means of pipetting method with a solution of 90 wt % pacliltaxel in ethanol and 10 wt % compound 4. Subsequently, the catheter balloon is dried with slow rotation at room temperature.

Example 5: Coating a Catheter Balloon with Paclitaxel and Compound 5

A catheter balloon is rotatably mounted on a horizontal rod and coated by means of pipetting method with a solution of 83 wt % pacliltaxel in ethanol and 17 wt % compound 5. Subsequently, the catheter balloon is dried with slow rotation at room temperature.

Example 6: Coating a Catheter Balloon with Paclitaxel and Compound 6

A catheter balloon is rotatably mounted on a horizontal rod and coated by means of spraying method with a solution of 95 wt % pacliltaxel in acetone and 5 wt % compound 6. Subsequently, the catheter balloon is dried with slow rotation at room temperature.

Example 7: Coating a Catheter Balloon with Paclitaxel and Compound 7

A fold balloon in deflated state is rotatably mounted on a horizontal rod and the folds of balloon are coated by means of pipetting method with a solution of 90 wt % pacliltaxel in ethanol and 10 wt % compound 7. Subsequently, the balloon is dried with slow rotation at room temperature under vacuum.

Example 8: Coating a Catheter Balloon with Paclitaxel and Compound 8

A catheter balloon is rotatably mounted on a horizontal rod and coated by means of spraying method with a solution of 90 wt % pacliltaxel in acetone and 10 wt % transport promoting molecular dispersant compound 8. Subsequently, the catheter balloon is dried with slow rotation at room temperature.

Example 9: Coating a Catheter Balloon with Paclitaxel and Compound 9

A catheter balloon is rotatably mounted on a horizontal rod and coated completely by means of spraying method with a solution of 86 wt % pacliltaxel in acetone and 14 wt % compound 9. Subsequently, the catheter balloon is dried with slow rotation at room temperature under vacuum.

Example 10: Coating a Catheter Balloon with Paclitaxel and Compound 10

A catheter balloon is rotatably mounted on a horizontal rod and coated completely by means of drag method with a solution of 60 wt % pacliltaxel in acetone and 40 wt % compound 10. Subsequently, the catheter balloon is dried with slow rotation at room temperature.

Example 11: Coating a Catheter Balloon with Paclitaxel and Compound 11

A catheter balloon is dipped into a solution of 40 wt % Pacliltaxel in DMSO and 60 wt % compound 11. Subsequently, the catheter balloon is dried with slow rotation at room temperature under vacuum.

Example 12: Coating a Catheter Balloon with Paclitaxel and Compound 12

A catheter balloon is rotatably mounted on a horizontal rod and coated completely by means of drag method with a solution of 80 wt % pacliltaxel in acetone and 20 wt % compound 12. Subsequently, the catheter balloon is dried with slow rotation at room temperature.

Example 13: Coating a Catheter Balloon with Paclitaxel and Compound 13

A catheter balloon is rotatably mounted on a horizontal rod and coated completely by means of spraying method with a solution of 90 wt % pacliltaxel in acetone and 10 wt % compound 13. Subsequently, the catheter balloon is dried with slow rotation at room temperature.

Example 14: Coating a Catheter Balloon with Paclitaxel and Compound 14

A catheter balloon is rotatably mounted on a horizontal rod and coated completely by means of pipetting method with a solution of 91 wt % pacliltaxel in acetone and 9 wt % compound 14. Subsequently, the catheter balloon is dried with slow rotation at room temperature.

Example 15: Coating a Catheter Balloon with Paclitaxel and Compound 15

A catheter balloon is rotatably mounted on a horizontal rod and coated completely by means of spreading method with a solution of 89 wt % pacliltaxel in acetone and 11 wt % compound 15. Subsequently, the catheter balloon is dried with slow rotation at room temperature.

Example 16: Coating a Catheter Balloon with Paclitaxel and Compound 16

A catheter balloon is rotatably mounted on a horizontal rod and coated completely by means of spraying method with a solution of 90 wt % pacliltaxel in acetone and 10 wt % compound 16. Subsequently, the catheter balloon is dried with slow rotation at room temperature.

Example 17: Coating a Catheter Balloon with Paclitaxel and Compound 17

A catheter balloon is rotatably mounted on a horizontal rod and coated completely by means of spreading method with a solution of 90 wt % pacliltaxel in acetone and 10 wt % compound 17. The coating procedure is repeated 2 more times. Subsequently, the catheter balloon is dried with slow rotation at room temperature.

Example 18: Coating a Catheter Balloon with Paclitaxel and Compound 18

A catheter balloon is rotatably mounted on a horizontal rod and coated completely by means of spraying method with a solution of 90 wt % pacliltaxel in acetone and 10 wt % compound 18. Subsequently, the catheter balloon is dried with slow rotation at room temperature.

Example 19: Coating a Catheter Balloon with Paclitaxel and Compound 19

A catheter balloon is rotatably mounted on a horizontal rod and coated completely by means of brushing procedure with a solution of 90 wt % pacliltaxel in acetone and 10 wt % compound 19. Subsequently, the catheter balloon is dried with slow rotation at room temperature.

Example 20: Coating a Catheter Balloon with Rapamycin and Compound 1

A catheter balloon is rotatably mounted on a horizontal rod and coated completely by means of spraying method with a solution of 90 wt % rapamycin in ethyl acetate and 10 wt % compound 1. Subsequently, the catheter balloon is dried with slow rotation at room temperature.

Example 21: Coating a Catheter Balloon with Rapamycin and a Mixture of Compound 2 and 3

A catheter balloon is coated completely in a solution of 90 wt % rapamycin in ethyl acetate and 5 wt % the transport promoting molecular dispersant according to compound 2 and 5 wt % compound 3. Subsequently, the catheter balloon is dried with slow rotation at room temperature.

Example 22: Coating a Catheter Balloon with a Mixture of Paclitaxel, Rapamycin and Compound 4

A catheter balloon is coated completely with a solution of 45 wt % paclitaxel, 45 wt % rapamycin in ethyl acetate and 10 wt % compound 4. Subsequently, the catheter balloon is dried with slow rotation at room temperature under vacuum.

Example 23: Coating a Catheter Balloon with a Crimped Stent with a Paclitaxel and Compound 5

A catheter balloon is rotatably mounted on a horizontal rod and coated by means of spraying method with a solution of 90 wt % paclitaxel in ethanol and 10 wt % compound 5. Subsequently, the catheter balloon is dried with slow rotation at room temperature. On this coated catheter balloon a stent made of polylactide is then crimped, which is coated likewise with a solution of 90 wt % paclitaxel in ethanol and 10 wt % compound 5.

Example 24: Use of a Catheter Balloon in Stenotic Vessels of Pigs

The effectiveness of catheter balloons with a coating of 90 wt % paclitaxel and 10 wt % compounds 1-19 was tested in animal experiments with pigs in overstretched coronary arteries.

Up to three coronary arteries (left circumflex artery, left anterior descending artery, right coronary artery) per pig were dilated. Per study group 10 coronary arteries are treated and the results averaged over all vessels. The results are summarized in Table 2. The term "late lumen loss" refers to the difference between the diameters of a vascular segment after dilation and of a follow-up angiogramm recorded after 28 days. In addition, the success of the application in histopathologic examination was analyzed.

TABLE 2

|  | overstretching rate (%) | Degree of stenosis 28 d (%) | late lumen loss (mm) |
| --- | --- | --- | --- |
| Uncoated | ca. 10 | 40.4 ± 12.5 | 1.24 ± 0.35 |
| Compound 1 + Ptx | ca. 10 | 14.8 ± 2.8 | 0.19 ± 0.15 |
| Compound 2 + Ptx | ca. 10 | 13.3 ± 1.7 | 0.18 ± 0.13 |
| Compound 3 + Ptx | ca. 10 | 15.8 ± 2.5 | 0.19 ± 0.14 |
| Compound 4 + Ptx | ca. 10 | 14.7 ± 3.6 | 0.17 ± 0.12 |
| Compound 5 + Ptx | ca. 10 | 16.3 ± 3.2 | 0.22 ± 0.15 |
| Compound 6 + Ptx | ca. 10 | 15.6 ± 3.8 | 0.20 ± 0.12 |
| Compound 7 + Ptx | ca. 10 | 13.8 ± 3.3 | 0.22 ± 0.11 |
| Compound 8 + Ptx | ca. 10 | 15.8 ± 2.1 | 0.16 ± 0.15 |
| Compound 9 + Ptx | ca. 10 | 14.8 ± 2.3 | 0.21 ± 0.11 |
| Compound 10 + Ptx | ca. 10 | 13.4 ± 3.2 | 0.21 ± 0.15 |
| Compound 11 + Ptx | ca. 10 | 12.1 ± 1.9 | 0.19 ± 0.10 |
| Compound 12 + Ptx | ca. 10 | 17.4 ± 3.2 | 0.17 ± 0.14 |
| Compound 13 + Ptx | ca. 10 | 15.3 ± 4.1 | 0.18 ± 0.15 |
| Compound 14 + Ptx | ca. 10 | 16.3 ± 3.7 | 0.22 ± 0.12 |
| Compound 15 + Ptx | ca. 10 | 10.2 ± 3.4 | 0.21 ± 0.13 |
| Compound 16 + Ptx | ca. 10 | 14.8 ± 5.3 | 0.21 ± 0.14 |
| Compound 17 + Ptx | ca. 10 | 16.8 ± 3.8 | 0.22 ± 0.12 |
| Compound 18 + Ptx | ca. 10 | 15.5 ± 3.2 | 0.18 ± 0.12 |
| Compound 19 + Ptx | ca. 10 | 14.9 ± 2.5 | 0.17 ± 0.10 |

Restenosis data of the experiments with catheter balloons coated with the compounds 1-19 showed after 28 days much lower values than those of the catheter balloons without an inventive coating. The inventive coating clearly enhanced the absorption of paclitaxel in the vessel walls and significantly reduced the restenosis rate in comparison to control.

Example 25: Preparation of a Stock Solution of the Agent with the Transport Promoting Molecular Dispersant Agent and the transport promoting molecular dispersant are dissolved in a ratio of 90 wt % to 10 wt % in acetone and the solution is mixed with stirring.

The invention claimed is:

1. Catheter balloon with or without crimped stent, wherein the surface of the catheter balloon is coated at least partially with at least one antirestenotic agent and at least one compound of general formula (I):

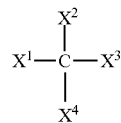

wherein $X^1$ represents one of the following residues
-$L^1$-$R^{18}$, —Y-$L^1$-$R^{18}$,
—Y—C($R^3$)($R^4$)-$L^1$-$R^{18}$,
-$L^1$-Y—C($R^3$)($R^4$)—$R^{18}$,   -$L^1$-C($R^3$)($R^4$)—Y—$R^{18}$,
—C($R^3$)($R^4$)—Y-$L^1$-C($R^5$)($R^6$)—$R^{18}$,   —C($R^3$)($R^4$)-$L^1$-Y—C($R^5$)($R^6$)—$R^{18}$;

$X^2$ represents one of the following residues
—$R^7$, —$CH_2$—$R^7$, or —O—$CH_2$—$R^7$;

$X^3$ represents one of the following residues
-$M^1$-$R^{26}$, -$M^1$-$(M^2)_r$-$M^3$-$R^{26}$, -$M^1$-$(M^2)_r$-$M^3$-$(M^4)_s$-$R^{26}$;

$X^4$ represents one of the following residues
-$L^2$-C($R^{10}$)($R^{11}$)—$R^{19}$, —C($R^{10}$)($R^{11}$)—C($R^{12}$)($R^{13}$)-$L^2$-$R^{19}$, —C($R^{10}$)($R^{11}$)-$L^2$-C($R^{12}$)($R^{13}$)—$R^{19}$, -$L^2$-C($R^{10}$)($R^{11}$)—C($R^{12}$)($R^{13}$)—$R^{19}$;

$L^1$ represents one of the following groups

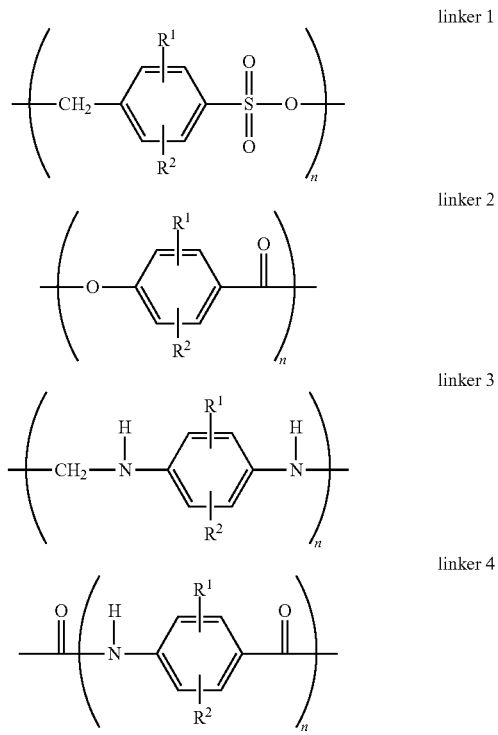

-continued

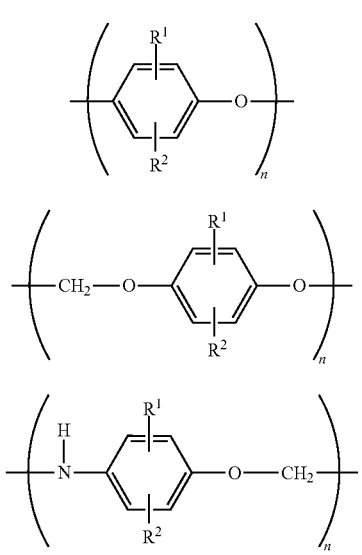
linker 5 linker 8 linker 9

$L^2$ represents one of the following groups
—O—CO—, —NH—CO—, —CO—, —CO—O—, or —CO—NH—;
$M^1$ represents one of the following groups

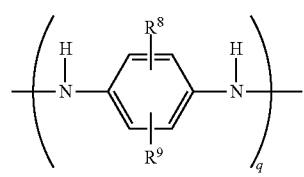
group 1

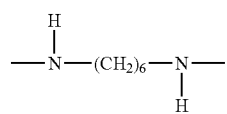
group 2

$M^2$ represents one of the following groups
—CH$_2$—, —O—CO—CH$_2$—CH$_2$—, or —CO—CH$_2$—CH$_2$—;
$M^3$ represents one of the following groups
a bond, —CO—, —NH—, —NH—CO—;
$M^4$ represents one of the following groups
(—O—CH$_2$—CH$_2$-)$_t$, (—CH$_2$—CH$_2$—O—)$_t$;
Y represents (—CH$_2$—)$_m$, (—CH$_2$—O—)$_m$, (~O—CH$_2$—)$_m$, or (—CH$_2$—CH$_2$—O—)$_m$;
$R^1$ to $R^6$ represent hydrogen;
$R^7$ to $R^{13}$ represent independently of each other the following residues: —$R^{14}$ to —$R^{30}$, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —O—CO—$R^{14}$, —N(CH$_3$)$_2$;
$R^{14}$ to $R^{30}$ represent independently of each other the following residues:
—CH$_2$—CF$_3$, cyclo-C$_3$H$_5$, cyclo-C$_4$H$_7$, cyclo-C$_5$H$_9$, —H, —CH$_3$, —C$_2$H$_5$, —C$_3$H$_7$, —CH(CH$_3$)$_2$, —C$_4$H$_9$, —C$_5$H$_{11}$, —C$_6$H$_{13}$;
m is an integer from 1 to 4;
n represents 0 or 1;
q represents 0 or 1;
r represents 0 or 1;
s represents 0 or 1;
t is an integer from 1 to 4;
wherein the compound according to general formula (I) has a molar mass (molecular weight) of at least 460 g/mol;
a boiling point of at least 500° C. (at atmospheric pressure);
a density from 0.95 g/cm$^3$ to 1.05 g/cm$^3$;
a flash point of above 100° C.; and
a refractive index $n_D^{20}$ between 1.440 and 1.460;
wherein the at least one antirestenotic agent is embedded or stored in the compound of the general formula (I), and
wherein the at least one antirestenotic agent is paclitaxel.

2. Catheter balloon according to claim 1, wherein the amount ratio of the antirestenotic agent and the at least one compound of general formula (I) is from 90 wt % antirestenotic agent to 10 wt % compound of general formula (I) to 10 wt % antirestenotic agent to 90 wt % compound of general formula (I).

3. Method for the preparation of a catheter balloon according to claim 1 comprising the steps of:
a) providing a catheter balloon of a balloon catheter;
b) providing a coating solution of the paclitaxel and the at least one compound of general formula (I) in a solvent or solvent mixture;
c) coating of the catheter balloon with the coating solution by means of dipping, spreading, spraying, brushing or pipetting procedure; and
d) drying the applied coating.

4. Catheter balloon with or without crimped stent, wherein the surface of the catheter balloon is coated at least partially with a mixture of an antirestenotic agent and at least one compound of general formula (I):

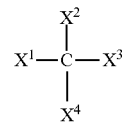

wherein the antirestenotic agent is homogenously dispersed in the at least one compound of general formula (I) in molecular form or as a particle with a particle sizes of less than 1 nm,
wherein the at least one compound of general formula (I) and the antirestenotic agent do not chemically react with each other,
wherein the the antirestenotic agent is is paclitaxel,
wherein the at least one compound of general formula (I) has a molar mass (molecular weight) of at least 460 g/mol, a density from 0.95 g/cm$^3$ to 1.05 g/cm$^3$, a flash point of above 100° C., and a refractive index $n_D^{20}$ between 1.440 and 1.460,
wherein
$X^1$ represents one of the following residues
-L$^1$-R$^{18}$, —Y—C(R$^3$)(R$^4$)-L$^1$-R$^{18}$, -L$^1$-Y—C(R$^3$)(R$^4$)—R$^{18}$,
-L$^1$-C(R$^3$)(R$^4$)—Y—R$^{18}$, —C(R$^3$)(R$^4$)—Y-L$^1$-C(R$^5$)(R$^6$)—R$^{18}$,
—C(R$^3$)(R$^4$)-L$^1$-Y—C(R$^5$)(R$^6$)—R$^{18}$;
$X^2$ represents one of the following residues
—R$^7$, —CH$_2$—R$^7$, or —O—CH$_2$—R$^7$;
$X^3$ represents one of the following residues
-M$^1$-R$^{26}$, -M$^1$-(M$^2$)$_r$-M$^3$-R$^{26}$, -M$^1$-(M$^2$)$_r$-M$^3$-(M$^4$)$_s$-R$^{26}$;

$X^4$ represents one of the following residues
-$L^2$-C($R^{10}$)($R^{11}$)—$R^{19}$, —C($R^{10}$)($R^{11}$)—C($R^{12}$)($R^{13}$)-$L^2$-$R^{19}$, —C($R^{10}$)($R^{11}$)-$L^2$-C($R^{12}$)($R^{13}$)—$R^{19}$, -$L^2$-C($R^{10}$)($R^{11}$)—C($R^{12}$)($R^{13}$)—$R^{19}$;

$L^1$ represents one of the following groups linker 1
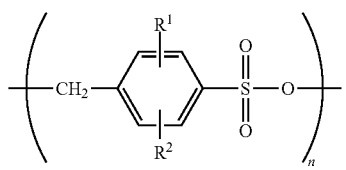

linker 2
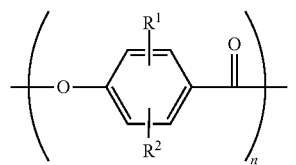

linker 3
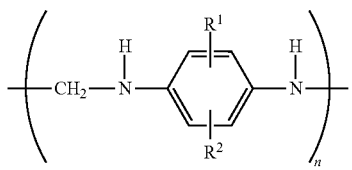

linker 4
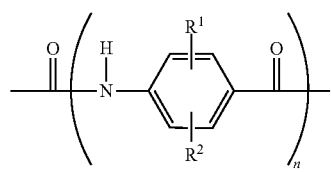

linker 5
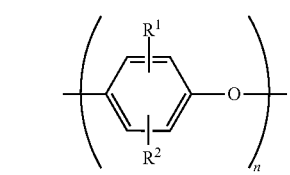

linker 8
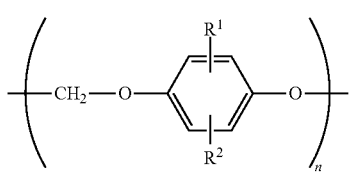

linker 9
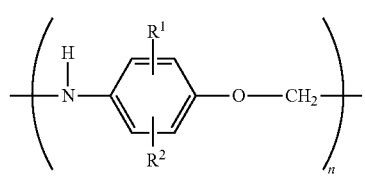

$L^2$ represents one of the following groups
—O—CO—, —NH—CO—, —CO—, —CO—O—, or —CO—NH—;

$M^1$ represents one of the following groups group 1
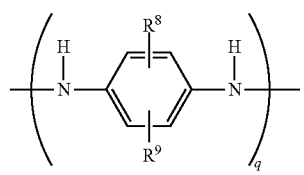

group 2
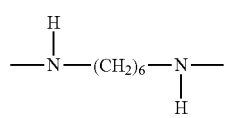

$M^2$ represents one of the following groups
CH$_2$—, —O—CO—CH$_2$—CH$_2$—, or —CO—CH$_2$—CH$_2$—;

$M^3$ represents one of the following groups
a bond, —CO—, —NH—, —NH—CO—;

$M^4$ represents one of the following groups
(—O—CH$_2$—CH$_2$-)$_r$, (—CH$_2$—CH$_2$—O—)$_t$;

Y represents (—CH$_2$—)$_m$, (—CH$_2$—O—)$_m$, (~O—CH$_2$—)$_m$, or (—CH$_2$—CH$_2$—O—)$_m$;

$R^1$ to $R^6$ represent hydrogen;

$R^7$ to $R^{13}$ represent independently of each other the following residues: —$R^{14}$ to —$R^{30}$, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —O—CO—$R^{14}$, —N(CH$_3$)$_2$;

$R^{14}$ to $R^{30}$ represent independently of each other the following residues:
—CH$_2$—CF$_3$, cyclo-C$_3$H$_5$, cyclo-C$_4$H$_7$, cyclo-C$_5$H$_9$, —H, —CH$_3$, —C$_2$H$_5$, —C$_3$H$_7$, —CH(CH$_3$)$_2$, —C$_4$H$_9$, —C$_5$H$_{11}$, —C$_6$H$_{13}$;

m is an integer from 1 to 4;
n represents 0 or 1;
q represents 0 or 1;
r represents 0 or 1;
s represents 0 or 1; and
t is an integer from 1 to 4.

5. Catheter balloon according to claim 1,
wherein the at least one compound of general formula (I) contains 7 to 9 oxygen atoms,
wherein compounds of general formula (I) with at least one amino group or amide group contain between 33 to 42 carbon atoms, and
wherein nitrogen-free compounds of general formula (I) contain between 24 to 36 carbon atoms.

6. Catheter balloon with or without crimped stent, wherein the surface of the catheter balloon is coated at least partially with at least one antirestenotic agent and at least one compound of general formula (I):

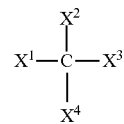

wherein
$X^1$ represents one of the following residues
-$L^1$-$R^{18}$, —Y-$L^1$-$R^{18}$, —Y—C(R³)(R⁴)-L¹-R¹⁸,
-L¹-Y—C(R³)(R⁴)—R¹⁸,   -L¹-C(R³)(R⁴)—Y—R¹⁸,
—C(R³)(R⁴)—Y-L¹-C(R⁵)(R⁶)—R¹⁸,   —C(R³)(R⁴)-L¹-Y—C(R⁵)(R⁶)—R¹⁸;

X² represents one of the following residues
—R⁷, —CH₂—R⁷, or —O—CH₂—R⁷;

X³ represents one of the following residues
-M¹-R²⁶, -M¹-(M²)$_r$-M³-R²⁶, -M¹-(M²)$_r$-M³-(M⁴)$_s$-R²⁶;

X⁴ represents one of the following residues
-L²-C(R¹⁰)(R¹¹)—R¹⁹, —C(R¹⁰)(R¹¹)—C(R¹²)(R¹³)-L²-R¹⁹, —C(R¹⁰)(R¹¹)-L²-C(R¹²)(R¹³)—R¹⁹, -L²-C(R¹⁰)(R¹¹)—C(R¹²)(R¹³)—R¹⁹;

L¹ represents one of the following groups

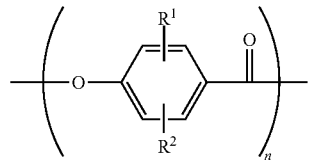
linker 2

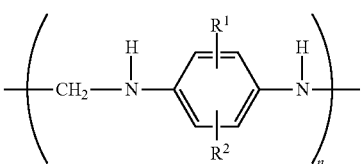
linker 3

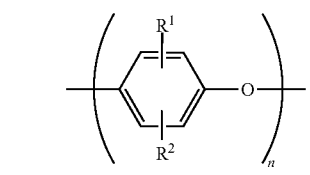
linker 5

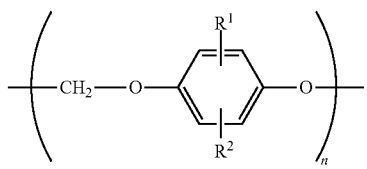
linker 8

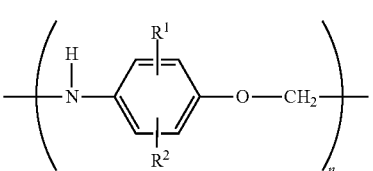
linker 9

L² represents one of the following groups
—O—CO—, —CO—, or —CO—O—;

M¹ represents one of the following groups

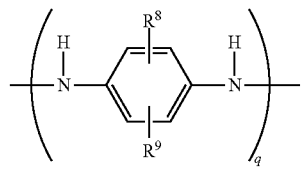
group 1

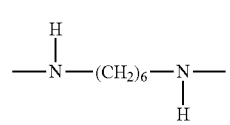
group 2

M² represents one of the following groups
CH₂—, —O—CO—CH₂—CH₂—, or —CO—CH₂—CH₂—;

M³ represents one of the following groups
a bond, —CO—, —NH—;

M⁴ represents one of the following groups
(—O—CH₂—CH₂-)$_t$, (—CH₂—CH₂—O—)$_t$;

Y represents (—CH₂—)$_m$, (—CH₂—O—)$_m$, (—O—CH₂—)$_m$, or (—CH₂—CH₂—O—)$_m$;

R¹ to R⁶ represent hydrogen;

R⁷ to R¹³ represent independently of each other the following residues: —R¹⁴ to —R³⁰, —OCH₃, —OC₂H₅, —OC₃H₇, —O-cyclo-C₃H₅, —OCH(CH₃)₂, —OC(CH₃)₃, —OC₄H₉, —COOCH₃, —COOC₂H₅, —COOC₃H₇, —COO-cyclo-C₃H₅, —COOCH(CH₃)₂, —COOC(CH₃)₃, —O—CO—R¹⁴, —N(CH₃)₂;

R¹⁴ to R³⁰ represent independently of each other the following residues:
—CH₂—CF₃, cyclo-C₃H₅, cyclo-C₄H₇, cyclo-C₅H₉, —H, —CH₃, —C₂H₅, —C₃H₇, —CH(CH₃)₂, —C₄H₉, —C₅H₁₁, —C₆H₁₃;

m is an integer from 1 to 4;
n represents 0 or 1;
q represents 0 or 1;
r represents 0 or 1;
s represents 0 or 1;
t is an integer from 1 to 4; and
wherein the compound according to general formula (I) has a molar mass (molecular weight) of at least 460 g/mol;
a boiling point of at least 500° C. (at atmospheric pressure);
a density from 0.95 g/cm³ to 1.05 g/cm³;
a flash point of above 100° C.; and
a refractive index $n_D^{20}$ between 1.440 and 1.460;
wherein the at least one antirestenotic agent is embedded or stored in the compound of the general formula (I),
wherein the at least one antirestenotic agent is paclitaxel, and
wherein the oxygen atoms are present in ester bonds or ether bonds.

* * * * *

UNITED STATES PATENT AND TRADEMARK OFFICE
CERTIFICATE OF CORRECTION

Page 1 of 1

PATENT NO.           : 11,185,614 B2
APPLICATION NO.      : 13/700175
DATED                : November 30, 2021
INVENTOR(S)          : Erika Hoffmann, Michael Hoffmann and Roland Horres It is certified that error appears in the above-identified patent and that said Letters Patent is hereby corrected as shown below:

In the Specification

Column 3, Line 53, change "Tillable" to -- fillable --.

Signed and Sealed this
Eighth Day of February, 2022

Drew Hirshfeld
*Performing the Functions and Duties of the*
*Under Secretary of Commerce for Intellectual Property and*
*Director of the United States Patent and Trademark Office*